US007157568B1

(12) United States Patent
Bhat et al.

(10) Patent No.: US 7,157,568 B1
(45) Date of Patent: Jan. 2, 2007

(54) HUMAN ESTROGEN RECEPTOR-β

(75) Inventors: Ramesh A. Bhat, King of Prussia, PA (US); Ruth Henderson, Swarthmore, PA (US); Chulai Hsiao, Wilmington, DE (US); Sotirios A. Karathanasis, Berwyn, PA (US)

(73) Assignee: American Home Products Corporation, Madison, NJ (US)

( * ) Notice: Subject to any disclaimer, the term of this patent is extended or adjusted under 35 U.S.C. 154(b) by 1311 days.

(21) Appl. No.: 08/906,365

(22) Filed: Aug. 5, 1997

(51) Int. Cl.
*C07H 21/04* (2006.01)
*C12N 15/63* (2006.01)
*C12N 15/09* (2006.01)

(52) U.S. Cl. .................. 536/23.5; 435/69.1; 435/69.7; 435/235.1; 435/325; 435/320.1; 435/170; 435/252.3; 435/455; 530/350

(58) Field of Classification Search ............... 435/69.1, 435/70.1, 320.1, 325, 72.1, 235; 530/350
See application file for complete search history.

(56) References Cited

U.S. PATENT DOCUMENTS 6,680,368 B1 * 1/2004 Mosselman et al. ........ 530/350

FOREIGN PATENT DOCUMENTS

| | | |
|---|---|---|
| EP | 0 798 378 | 10/1997 |
| WO | WO 99/12961 | 3/1989 |
| WO | WO97/09348 | 3/1997 |
| WO | WO 99/11760 | 3/1999 |

OTHER PUBLICATIONS

Kuiper et al., *Proc.Natl.Acad.Sci.USA 93*:5925, 1996.
Mosselman et al., *FEBS Letts. 392*:49, 1996.
Matteucci et al., 1981, *J. Am. Chem. Soc.* 103:3185.
Yoo et al., 1989, *J. Biol. Chem.* 764:17078.
Merrifield, 1963, *J. Am. Chem. Soc.* 85:2149.
Mayer and Walker, 1987, *Immunochemical Methods in Cell and Molecular Biology*, (Academic Press, London).
Moore et al., GenBank Accession No. AF051427(Jul. 14, 1999; submitted Feb. 25, 1998)( referencing Biochem. Biophys. Res. Commun. (1998), 274(1): 75-78).
Ogawa, S., "Direct Submission," GenBank Accession No. AB006590 (Feb. 5, 1999; submitted Aug. 13, 1997)(referencing Biochem. Biophys. Res. Commun. 1998), 243(1): 122-126).
Li, L.C. et al., GenBank Accession No. AF191544 (Jan. 12, 2000; submitted Oct. 1, 1999)(referencing unpublished, submitted to Urology, Oct. 1, 1999).
Moore et al., GenBank Accession No. AF060555(Apr. 29, 1998: submitted Apr. 20, 1998)( referencing unpublished, submitted to Molecular Sciences, Apr. 20, 1998).
Lu et al., GenBank Accession No. AF124790(May 27, 1999; submitted Jan. 29, 1999)(referencing unpublished, submitted to Biochemistry, Jan. 29, 1999).
Moore et al., GenBank Accession No. AF051428 (Mar. 17, 1998; submitted Feb. 25, 1998) (referencing unpublished, submitted to Molecular Sciences, Feb. 25, 1998).
Sieste Mosselman, et al., ERβ Identification and Characterization of a Novel Human Estrogen Receptor, FEBS, vol. 3902/1, 49-53 (1996).

* cited by examiner

*Primary Examiner*—Gary B. Nickol
*Assistant Examiner*—Nirmal S. Basi
(74) *Attorney, Agent, or Firm*—Darby & Darby

(57) ABSTRACT

The present invention provides isolated nucleic acids encoding full-length human estrogen receptor-β (hERβ), which comprises 530 amino acids. The invention also provides isolated hERβ polypeptides and hERβ-reactive antibodies, including those that specifically recognize amino acids 1–45 of hERβ. The invention also encompasses methods for identifying hERβ-interactive compounds, including agonists, antagonists, and co-activators.

9 Claims, 8 Drawing Sheets

FIG. 3

```
CAGCCATTATACTTGCCCACGAATCTTTGAGAACATTATAATGACCTTTGTGCCTCTTCT   60
TGCAAGGTGTTTTCTCAGCTGCTATCTCAAGACATGGATATAAAAAACTCACCATCTAGC  120
CTTAATTCTCCTTCCTCCTACAACTGCAGTCAATCCATCTTACCCCTGGAGCACGGCTCC  180
ATATACATACCTTCCTCCTATGTAGACAGCCACCATGAATATCCAGCCATGACATTCTAT  240
AGCCCTGCTGTGATGAATTACAGCATTCCCAGCAATGTCACTAACTTGGAAGGTGGGCCT  300
GGTCGGCAGACCACAAGCCCAAATGTGTTGTGGCCAACACCTGGGCACCTTTCTCCTTTA  360
GTGGTCCATCGCCAGTTATCACATCTGTATGCGGAACCTCAAAAGAGTCCCTGGTGTGAA  420
GCAAGATCGCTAGAACACACCTTACCTGTAAACAGAGAGACACTGAAAAGGAAGGTTAGT  480
GGGAACCGTTGCGCCAGCCCTGTTACTGGTCCAGGTTCAAAGAGGGATGCTCACTTCTGC  540
GCTGTCTGCAGCGATTACGCATCGGGATATCACTATGGAGTCTGGTCGTGTGAAGGATGT  600
AAGGCCTTTTTTAAAAGAAGCATTCAAGGACATAATGATTATATTTGTCCAGCTACAAAT  660
CAGTGTACAATCGATAAAAACCGGCGCAAGAGCTGCCAGGCCTGCCGACTTCGGAAGTGT  720
TACGAAGTGGGAATGGTGAAGTGTGGCTCCCGGAGAGAGAGATGTGGGTACCGCCTTGTG  780
CGGAGACAGAGAAGTGCCGACGAGCAGCTGCACTGTGCCGGCAAGGCCAAGAGAAGTGGC  840
GGCCACGCGCCCCGAGTGCGGGAGCTGCTGCTGGACGCCCTGAGCCCCGAGCAGCTAGTG  900
CTCACCCTCCTGGAGGCTGAGCCGCCCCATGTGCTGATCAGCCGCCCCAGTGCGCCCTTC  960
ACCGAGGCCTCCATGATGATGTCCCTGACCAAGTTGGCCGACAAGGAGTTGGTACACATG 1020
ATCAGCTGGGCCAAGAAGATTCCCGGCTTTGTGGAGCTCAGCCTGTTCGACCAAGTGCGG 1080
CTCTTGGAGAGCTGTTGGATGGAGGTGTTAATGATGGGGCTGATGTGGCGCTCAATTGAC 1140
CACCCCGGCAAGCTCATCTTTGCTCCAGATCTTGTTCTGGACAGGGATGAGGGGAAATGC 1200
GTAGAAGGAATTCTGGAAATCTTTGACATGCTCCTGGCAACTACTTCAAGGTTTCGAGAG 1260
TTAAAACTCCAACACAAAGAATATCTCTGTGTCAAGGCCATGATCCTGCTCAATTCCAGT 1320
ATGTACCCTCTGGTCACAGCGACCCAGGATGCTGACAGCAGCCGGAAGCTGGCTCACTTG 1380
CTGAACGCCGTGACCGATGCTTTGGTTTGGGTGATTGCCAAGAGCGGCATCTCCTCCCAG 1440
CAGCAATCCATGCGCCTGGCTAACCTCCTGATGCTCCTGTCCCACGTCAGGCATGCGAGT 1500
AACAAGGGCATGGAACATCTGCTCAACATGAAGTGCAAAAATGTGGTCCCAGTGTATGAC 1560
CTGCTGCTGGAGATGCTGAATGCCCACGTGCTTCGCGGGTGCAAGTCCTCCATCACGGGG 1620
TCCGAGTGCAGCCCGGCAGAGGACAGTAAAAGCAAAGAGGGCTCCCAGAACCCACAGTCT 1680
CAGTGA  1686
```

FIG. 4

```
MDIKNSPSSL NSPSSYNCSQ SILPLEHGSI YIPSSYVDSH HEYPAMTFYS    50
PAVMNYSIPS NVTNLEGGPG RQTTSPNVLW PTPGHLSPLV VHRQLSHLYA   100
EPQKSPWCEA RSLEHTLPVN RETLKRKVSG NRCASPVTGP GSKRDAHFCA   150
VCSDYASGYH YGVWSCEGCK AFFKRSIQGH NDYICPATNQ CTIDKNRRKS   200
CQACRLRKCY EVGMVKCGSR RERCGYRLVR RQRSADEQLH CAGKAKRSGG   250
HAPRVRELLL DALSPEQLVL TLLEAEPPHV LISRPSAPFT EASMMMSLTK   300
LADKELVHMI SWAKKIPGFV ELSLFDQVRL LESCWMEVLM MGLMWRSIDH   350
PGKLIFAPDL VLDRDEGKCV EGILEIFDML LATTSRFREL KLQHKEYLCV   400
KAMILLNSSM YPLVTATQDA DSSRKLAHLL NAVTDALVWV IAKSGISSQQ   450
QSMRLANLLM LLSHVRHASN KGMEHLLNMK CKNVVPVYDL LLEMLNAHVL   500
RGCKSSITGS ECSPAEDSKS KEGSQNPQSQ   531
```

HUMAN ESTROGEN RECEPTOR-β

FIELD OF THE INVENTION

This invention pertains to DNA encoding a novel human estrogen receptor-β (hERβ), hERβ polypeptides, and methods for expressing and isolating hERβ. The invention also pertains to methods for using hERβ to identify coactivators and inhibitors as well as tissue-specific estrogens.

BACKGROUND OF THE INVENTION

The physiological response to steroid hormones is mediated by specific interactions of steroids with nuclear receptors, which are ligand-activated transcription factors that regulate the expression of target genes by binding to specific DNA response elements. These receptors comprise (in an aminoterminal-to-carboxyterminal direction) a hypervariable aminoterminal domain that contributes to the transactivation function; a highly conserved DNA-binding domain responsible for receptor dimerization and specific DNA binding; and a carboxyterminal domain involved in ligand-binding, nuclear localization, and ligand-dependent transactivation.

Recently, cDNA was cloned from rat prostate and was shown to have significant homology to a previously isolated rat estrogen receptor cDNA. Kuiper et al., *Proc.Natl.Acad.Sci.USA* 93:5925, 1996. This receptor was designated ERβ to distinguish it from a previously cloned receptor, ERα. Rat ERβ was shown to be expressed in the prostate, testes, ovary, and thymus, in contrast to ERα, which is most highly expressed in the uterus, breast, liver, and pituitary.

A human ERβ homologue having the aminoterminal sequence Gly-Tyr-Ser has been reported. Mosselman et al., *FEBS Letts.* 392:49, 1996. This reported sequence lacks an initiator methionine, however; therefore, the complete aminoterminal sequence could not be determined. Thus, the full-length human gene remained unknown and an accurate picture of the molecular determinants of the transactivation function of authentic hERβ could not be obtained.

SUMMARY OF THE INVENTION

The present invention provides nucleic acids encoding a full-length human estrogen receptor-β (hERβ$_L$). The nucleic acid sequence of hERβ$_L$, which is depicted in FIG. 3, SEQ ID NO:1, encodes a receptor having the amino acid sequence depicted in FIG. 4, SEQ ID NO:2. hERβ$_L$ according to the present invention contains 45 amino acids at its aminoterminus which were not previously known. These amino acids are believed to contribute to the transcription activation function of the receptor.

hERβ$_L$ is selectively expressed in the thymus, spleen, ovary, and testes. Accordingly, hERβ$_L$ can be used to identify co-activator proteins that are involved in estrogen-regulated gene expression, as well to identify tissue-selective estrogens.

The present invention provides isolated polypeptides having the sequence of SEQ ID NO:2 and function-conservative variants thereof which exhibit estrogen-regulated transcriptional activation activity. In a related aspect, the invention encompasses isolated peptides derived from hERβ comprising a sequence corresponding to amino acids 1–45 of SEQ ID NO:2 and function-conservative variants thereof, as explained above. It is believed that this sequence provides at least part of the transactivation function.

The present invention also provides isolated nucleic acids encoding hERβ$_L$ and hERβ$_L$-derived peptides, including the nucleic acid sequence depicted in FIG. 3, SEQ ID NO:1 and subfragments thereof encoding peptides which comprise amino acids 1–45, as well as sequence-conservative and function-conservative variants thereof. Also encompassed by the invention are DNA vectors comprising an hERβ$_L$-encoding sequence operably linked to a transcription regulatory element and cells comprising these vectors. Methods for producing hERβ$_L$-derived polypeptides include incubating a cell comprising an hERβ$_L$-encoding expression vector under conditions that permit expression of one or more hERβ polypeptides. The methods further include: (a) harvesting the cells to produce a cell fraction and a medium fraction; and (b) recovering the polypeptide(s) from the cell fraction, medium fraction, or both.

In another aspect, the invention provides methods for identifying hERβ-interactive compounds, including agonists, antagonists, and co-activator proteins. In one embodiment, the method includes:

(a) contacting purified hERβ with a labeled ligand in the presence of test compounds, to form test reactions, and in the absence of test compounds, to form control reactions;

(b) incubating the test and control reactions under appropriate conditions to achieve specific binding of the labelled ligand to hERβ;

(c) determining the level of binding of the labeled ligand to hERβ in said test and control cultures; and (d) identifying as a hERβ-interactive compound any compound that reduces the binding of the labeled ligand to hERβ.

BRIEF DESCRIPTION OF THE DRAWINGS

FIG. 3 is an illustration of the full-length cDNA sequence encoding human estrogen receptor-β (hERβ$_L$) (SEQ ID NO:1).

FIG. 4 is an illustration of the predicted amino acid sequence of the hERβ polypeptide (SEQ ID NO:2). The first 45 (previously unknown) amino acids are underlined.

DETAILED DESCRIPTION OF THE INVENTION

Human estrogen receptor-β (hereinafter, hERβ) comprises aminoterminal amino acid residues not previously known. The present invention encompasses isolated, purified, nucleic acids encoding authentic full-length hERβ of 530 amino acid residues and fragments thereof which include nucleic acids encoding amino acids 1–45 of hERβ. The invention also encompasses isolated, purified, polypeptides comprising hERβ and peptides derived therefrom, particularly peptides which include residues 1–45 of hERβ. The invention also provides expression systems in which transcriptionally active hERβ or fragments derived therefrom can be produced, as well as screening methods for identifying hERβ agonists and antagonists (including tissue-specific estrogens and anti-estrogens) as well as hERβ co-activators and inhibitors.

Isolation and Characterization of the Gene Encoding hERβ

The present inventors have isolated the cDNA encoding hERβ using the methods outlined below. Human testis Poly A+ RNA (1 μg, Clontech, Palo Alto Calif.) was mixed with 0.5 μg oligo dT primer (GIBCO-BRL, Gaithersburg Md.) in a total volume of 10 μl. The mixture was heated at 70° C. for 10 minutes, and, after cooling on ice, was supplemented with 500 μM of each deoxynucleoside triphosphate, 1× cDNA synthesis buffer, and 10 mM DTT to a final reaction volume of 20 μl. The mixture was incubated at 42° C. for 2.5 minutes and then supplemented with 1–2 units reverse transcriptase (GIBCO-BRL, Gaithersburg Md.), after which it was incubated at 45° C. for 30 minutes and 50° C. for 5 minutes. One-tenth of this mixture (approximately 2 μl) containing the cDNA template was then used in PCR amplification of hERβ using forward and reverse primers as described below.

Alignment of the known rat ERβ sequence (Kuiper et al., *Proc.Natl.Acad.Sci.USA* 93:5925, 1996) with that of a human homologue (Mosselman et al., *FEBS Letts*. 392:49, 1996) suggested that the human sequence lacked at least the ultimate and penultimate residues at its aminoterminus, as shown below:

Rat: MTFYSPAVMNYS . . . (SEQ ID NO:3)
Human: GYSPAVMNYS . . . (SEQ ID NO:4)

Based on this information, PCR primers were designed that supplement the human sequence with the two missing aminoterminal residues M and T and with an artificial Kozak translation initiation sequence. The forward primer, having the sequence (SEQ ID NO:5) 5'-GGAAGCTTGTCGACCATCATGACCGGCTATAGCCCTGCTGTGATG-3' and a reverse primer, having the sequence (SEQ ID NO:6) 5'-GGATCTAGAGTCGACGCGTCACTGAGACTGAGGGTTCTGG-3' were used to amplify hERβ sequences in a reaction containing the following components: 2 μl of the cDNA template described above; 1×PCR buffer; 200 μM of each deoxynucleoside triphosphate, 2 units of hot tab polymerase (Amersham, Arlington Heights Ill.), and 1 μg of each of the forward and reverse primers. The reaction mixture was heated to 95° C. for 2 minutes, annealed at 52° C. for 1 minute, and amplified using 36 cycles of 72° C. for 1.5 minutes.

Figure 1:
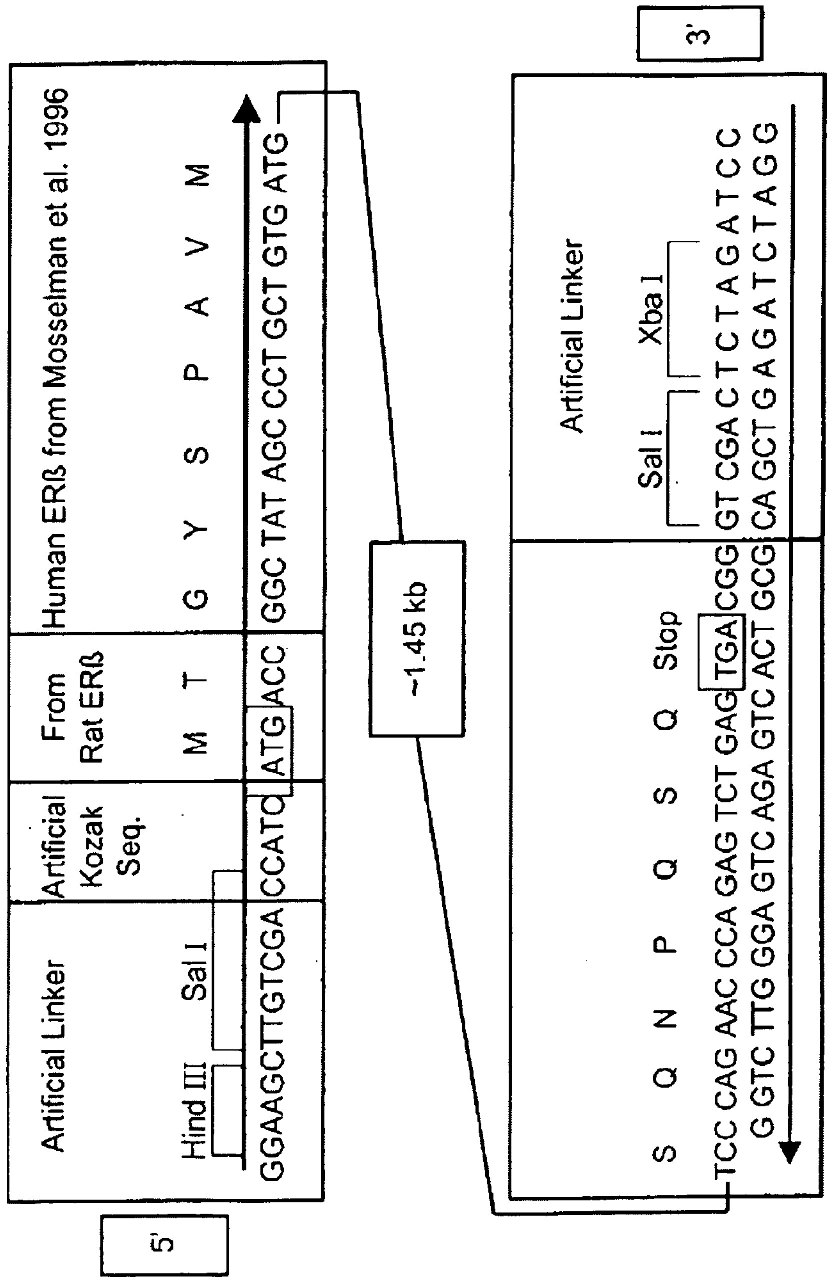
FIG. 1 is a schematic illustration of the oligonucleotides used for PCR amplification of human estrogen receptor-β (hERβ$_L$) cDNA (SEQ ID NO:5 and SEQ ID NO:6).
Figure 2:
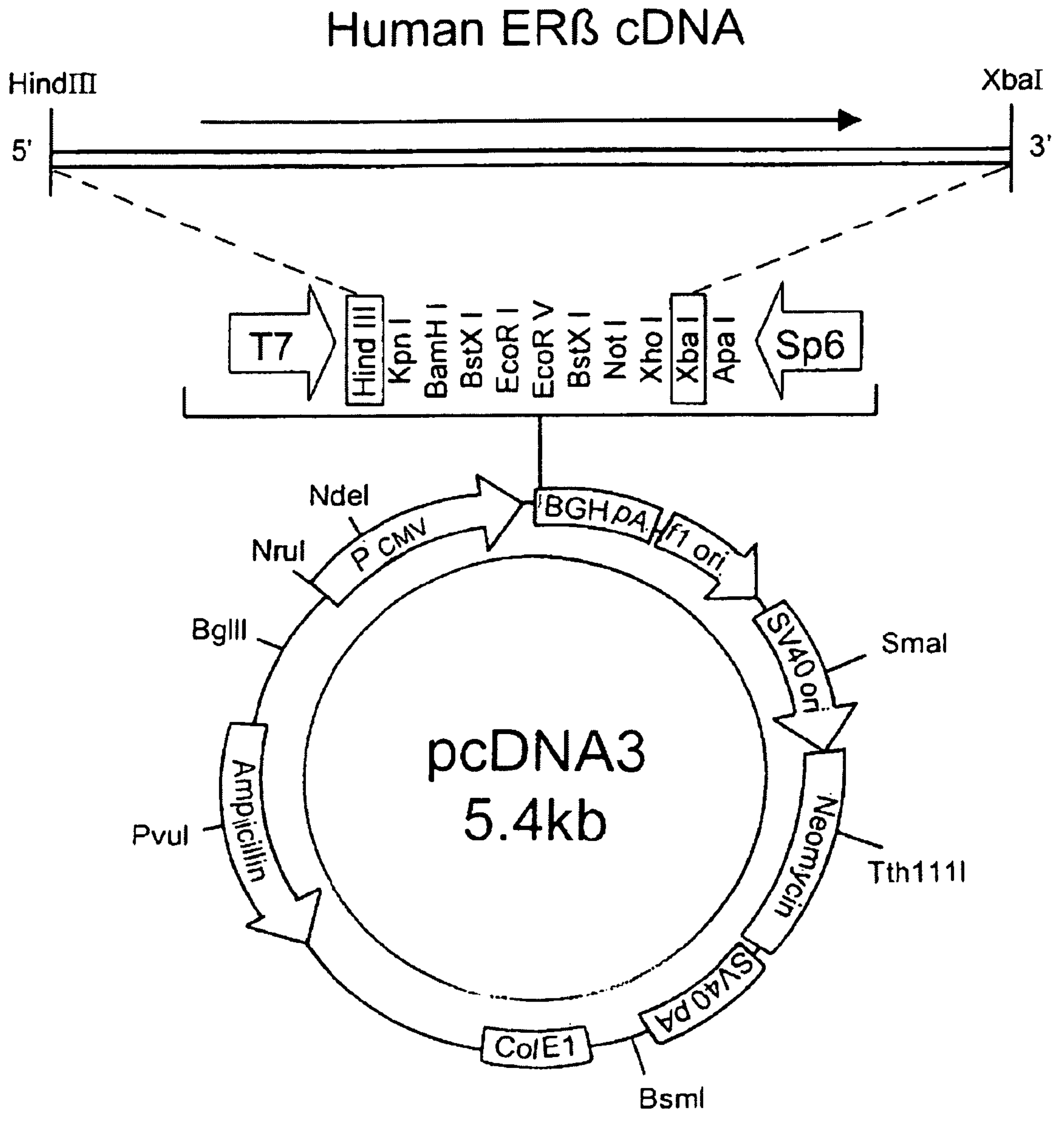
FIG. 2 is a schematic illustration of the pcDNA3 plasmid containing hERβ$_L$ cDNA.

A fragment of approximately 1500 bp in length was produced. The fragment digested with HindIII and XbaI (which cleave at sites present in the forward and reverse primer sequences, respectively, but not in the main body of the amplified cDNA sequence) and cloned into the corresponding sites of the pcDNA3 expression vector (Invitrogen, Carlsbad Calif.). This assymetric cloning strategy places the 5' end of hERβ cDNA under the control of the viral CMV promoter in pcDNA3 (FIGS. 1 and 2). Several insert-containing pcDNA3 clones were identified. Plasmid DNA was prepared from three clones using a plasmid purification kit (Qiagen, Santa Clarita Calif.) and their insert sequences were determined by the dideoxy termination method. One clone (designated R61010-2.24 or Clone 3) was found to contain an insert with a nucleotide sequence identical to the published hERβ sequence (Mosselman et al., *FEBS Letts*. 392:49, 1996) and had the following 5' end structure:

M T G Y . . . (SEQ ID NO:7)
CCATC ATG ACC GGC TAT . . . (SEQ ID NO:8)

This clone was designated "truncated hERβ" or hER$\beta_T$.

To verify the aminoterminal and upstream sequence of human hERβ, two independent approaches were taken, as described below.

(1) 10 μl of a human ovary 5'-Stretch cDNA library (Clontech, Palo Alto Calif.) was mixed with 50 μl of 1× K solution (1×PCR Buffer (GIBCO-BRL, Gaithersburg Md.), 2.5 mM $MgCl_2$, 0.5% Tween-20, 100 μg/ml Proteinase K), and the reaction mixture was incubated at 56° C. for 2 hours, then at 99° C. for 10 minutes. 5 μl of this reaction mixture were then used as template in a nested PCR reation. For the first round, the forward primer (pDR2 sequencing primer, Clontech, Palo Alto Calif.) had the sequence 5'-CTGGTAAGTTTAGTCTTTTTGTC-3' (SEQ ID NO:9), and the reverse primer (hERβ-specific, designated oligo #12908) had the sequence 5'-GCTTCACACCAAGGACTCTTTTGAG-3'(SEQ ID NO:10). The reaction contained 1× Klentaq PCR reaction buffer (40 mM Tricine-KOH, 15 mM KOAc, 3.5 mM $Mg(OAc)_2$, 75 μg/ml bovine serum albumin); 0.2 mM of each dNTP; 0.2 μM of each of the above primers, and 1 unit of Klentaq Polymerase Mix (Clontech, Palo Alto Calif.). Touchdown PCR conditions were as follows: 5 cycles of 94° C. for 2 seconds and 72° C. for 4 minutes, followed by 30 cycles of 94° C. for 2 seconds and 67° C. for 3 minutes.

Excess nucleotides and primers were removed from first round PCR reactions by purification over Wizard PCR columns (Promega, Madison Wis.). A second-round PCR reaction was then performed using 2 μl of the purified first-round reaction mixture. For the second round, the forward primer was the pDR2 sequencing primer shown above, and the reverse primer had the sequence 5'-GTTG-GCCACAACACATTTGGGCTTGT-3' (hERβ-specific, designated oligo #13871) (SEQ ID NO:11). The PCR reaction and cycling conditions were identical to those employed in the first round. The products were cloned into pCR2.1 (Invitrogen) and three resulting clones were sequenced. All three clones (designated L1, L2, and L3) contained hERβ inserts of different lengths, all of which were homologous to hERβ and to each other.

(2) A Marathon Ready thymus cDNA kit (Clontech) for 5' rapid amplification of cDNA ends (RACE) was also used to isolated hERβ 5' clones. In the first round of a nested PCR reaction, 51 μl of human thymus Marathon-ready cDNA (Clontech) was used as template. The forward primer had the sequence 5'-CCATCCTAATACGACTCACTAT-AGGGC-3' (Adaptorprimer 1, Clontech) (SEQ ID NO:12), and the reverse primer had the sequence 5'-GCTTCACAC-CAAGGACTCTTTTGAG-3' (hERβ-specific, designated oligo #12908) (SEQ ID NO:10). The PCR reaction and cycling conditions were identical to those described in (1) above.

Excess nucleotides and primers were removed from the first round PCR reactions by purification over Wizard PCR columns (Promega). A second round PCR reaction was performed using 2 μl of the purified first round reaction. For the second round, the forward primer had the sequence 5'-ACTCACTATAGGGCTCGAGCGGC-3' (nested adaptor primer 2, Clontech) (SEQ ID NO:13), and the reverse primer had the sequence 5'-GTTGGCCACAACACATTTGGGCT-TGT-3' (hERβ-specific, designated oligo #13971) (SEQ ID NO:11). The second round PCR reaction and cycling conditions were identical to those employed in the first round. The products were cloned into the pCR2.1 vector and two clones were sequenced. The two clones contain insert sequences of different lengths that are homologous to hERβ, to each other, and to the sequences isolated from a human ovary cDNA library as described above.

All of the hERβ sequences isolated by methods (1) and (2) above contained 110 nucleotides corresponding to hERβ$_T$ sequences, as well as 228 additional nucleotides at the 5' end (FIG. 3).

The hERβ cDNA sequence determined from these clones contained several important differences from the previously known human sequence. First, the third amino acid of the previous sequence was found to be F and not G (see above). Second, the methionine residue at the aminoterminus of the previous sequence was found not to be the initiator (i.e., true aminoterminal) residue. Rather, the authentic full-length hERβ cDNA sequence encodes a polypeptide having 530 residues, the first 45 of which are not found in the previously known human sequence (FIG. 4). The sequence appears to be quite homologous to rat ERβ; however, this reading frame was not identified previously (Kuiper et al., *Proc.Natl.Acad.Sci.USA* 93:5925, 1996). Furthermore, an optimal Kozak translation initiation sequence is found upstream of the newly discovered initiator methionine codon. A termination codon was identified 63 nucleotides upstream to the authentic ATG initiator codon in the same reading frame.

The cDNA encoding authentic full-length hERβ was cloned into pcDNA3 under the control of the CMV promoter; this expression vector was designated "long hERβ" or hERβ$_L$.

Synthesis of Full-Length hERβ and Truncated hERβ

Figure 5:
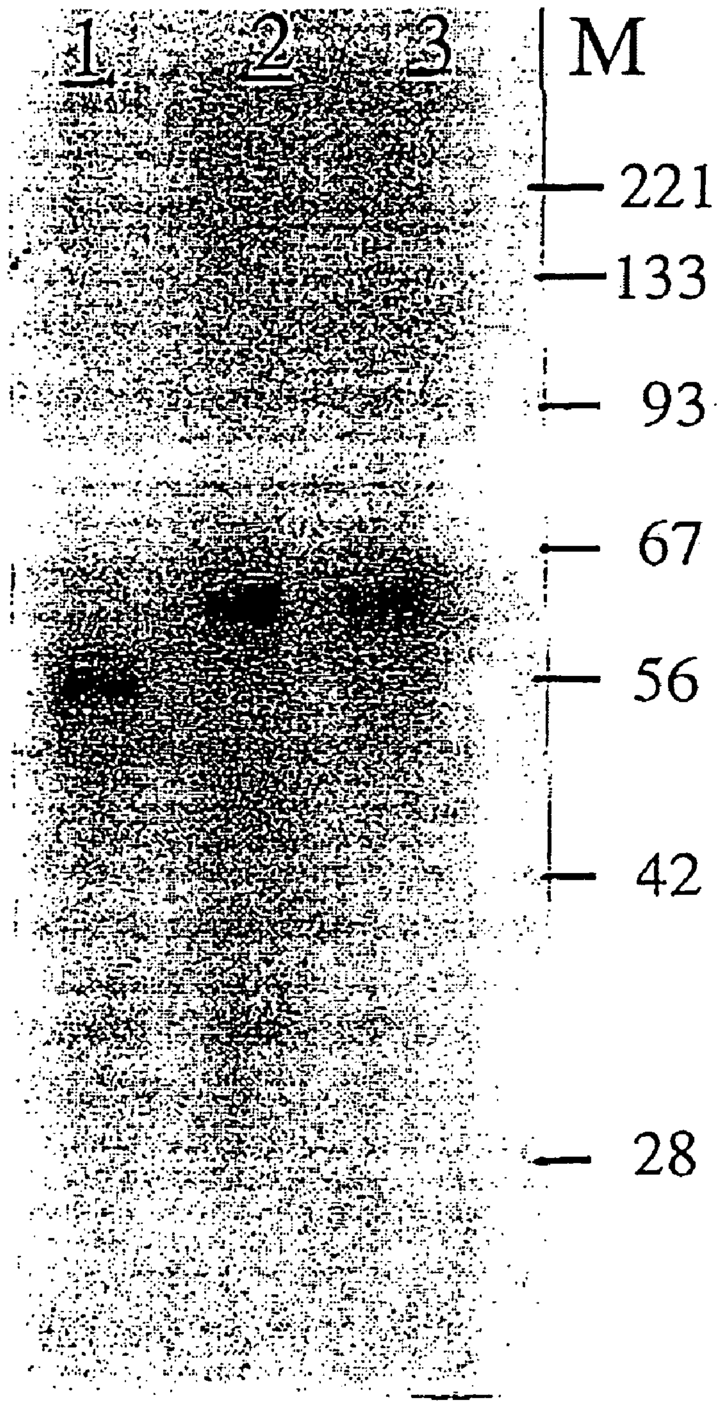
FIG. 5 is a photographic illustration of an autoradiogram of a 10% SDS-polyacrylamide gel in which hERβ in vitro translation products are resolved. Lane 1, hERβ$_T$; lane 2, hERβ$_L$ produced from a vector encoding a synthetic translation initiation site; lane 3, hERβ$_L$ produced from a vector encoding the natural hERβ translation initiation sequences.

To examine the natural start site for translation of hERβ, three plasmids were subjected to coupled transcription-translation, encoding hERβ$_T$ (with a synthetic upstream translation initiation sequence), hERβ$_L$ (with a synthetic upstream translation initiation sequence), and hERβ$_L$ containing 93 nucleotides of its native upstream sequence (the entire sequence shown in FIG. 3). The plasmids were transcribed and translated using the TNT T7 Coupled Reticulocyte Lysate System (Promega #L4610). Circular plasmid DNA was purified using Qiagen Maxi-Kit #12362. 2 μg of the DNA was transcribed and translated in a single reaction in the presence of [$^{35}$S]-methionine (New England Nuclear, Boston Mass.). The translation products were resolved on a 10% SDS polyacrylamide gel and were visualized by autoradiography (FIG. 5).

The resulting translation products of both hERβ$_L$ products were of similar size (~63 kDa), and the hERβ$_T$ product was appropriately shorter (~56 KDa). This indicates that the initiator ATG most likely utilized in vivo is the ATG at position 94–96. Utilization of a further upstream ATG is unlikely because of a termination codon in-fram with the presumed start site. Confirmation of the authentic start site is achieved by subjecting hERβ polypeptides to aminoterminal sequencing.

Functional Differences Between Full-Length hERβ and Truncated hERβ

The experiments described below were performed to evaluate the transcription activation properties of full-length hERβ according to the present invention and to compare it with that of truncated hERβ. hERβ$_L$ and hERβ$_T$ were expressed in parallel in different cell types and tested for their ability to transactivate reporter genes containing estrogen response elements (EREs). Alternatively, hERβ$_L$ and hERβ$_T$ may be expressed in host cells containing endogenous estrogen-responsive genes and the estrogen-mediated activation of the endogenous genes is measured.

(i) HepG2 Cells:

HepG2 cells (ATCC) were transfected in parallel with either pcDNA3-hERβ$_L$ or pcDNA3-hERβ$_T$ using the calcium phosphate co-precipitation method. Cells were co-transfected with a reporter plasmid containing a luciferase gene preceded by either an ERE upstream of the thymidine kinase (TK) basal promoter, or the TK basal promoter alone. Cells also received a plasmid encoding β-galactosidase under the control of an RSV promoter, which was used to correct for variation in DNA uptake. Five hours after transfection, cells were incubated with or without $10^{-6}$M 17-β estradiol for 20 hours, after which cell extracts were prepared. Luciferase activity was measured by a chemiluminescent method using the Promega luciferase assay system, and β-galactosidase activity was measured by Galactolight (Tropix, Inc., Bedford Mass.); luciferase activity was then normalized to β-galactosidase activity.

Figure 6A:
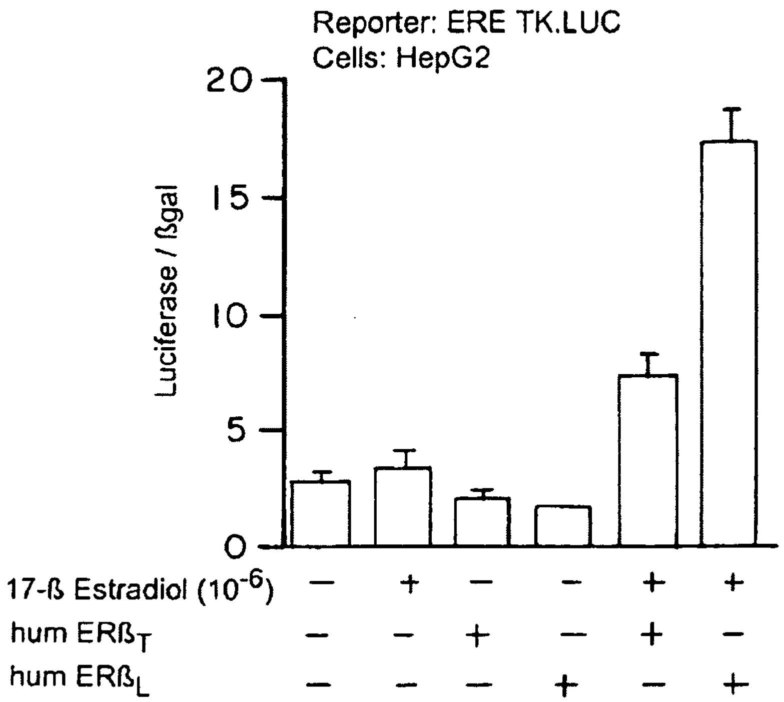
FIG. 6A is a graphic illustration of the transcriptional activation capacity of full-length hERβ (hERβ$_L$) and truncated hERβ (hERβ$_T$) expressed in HepG2 cells. Cells were transfected with either hERβ$_L$ or hERβ$_T$ and co-transfected with a luciferase reporter plasmid containing an estrogen response element (ERE) (ERE.TK.LUC) and a control β-galactosidase plasmid. Cells were incubated in the absence or presence of estradiol, after which luciferase activity was measured and normalized to β-galactosidase activity.
Figure 6B:
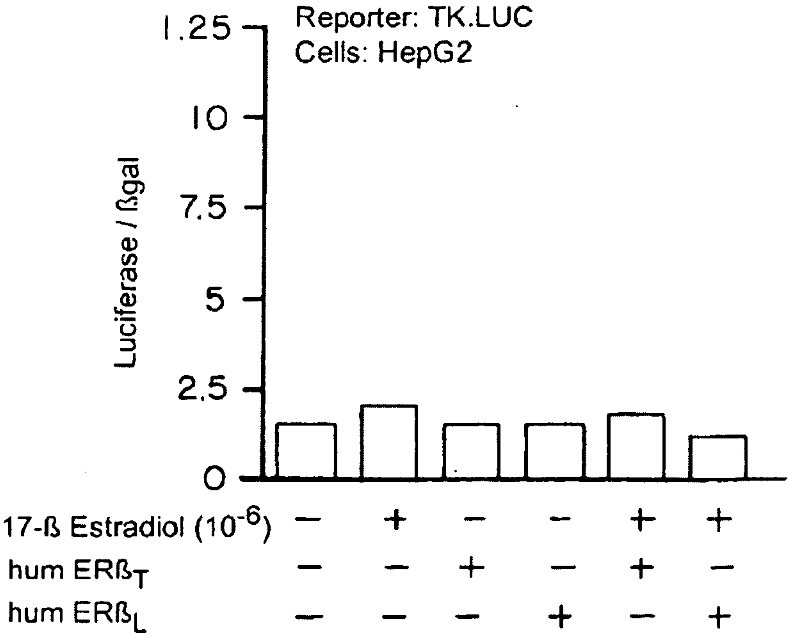
FIG. 6B is a graphic illustration of luciferase activity in HepG2 cells transfected with either hERβ$_L$ or hERβ$_T$ and co-transfected with a luciferase reporter plasmid lacking an ERE (TK.LUC)

The results shown in FIG. 6A indicate that, in the presence of estradiol, hERβ$_T$ caused a 2-fold stimulation of ERE activity. By contrast, hERβ$_T$ under the same conditions caused a 6-fold stimulation of ERE activity. Thus, hERβ$_L$ is about 3-fold more active than hERβ$_T$ in this circumstance.

Figure 7:
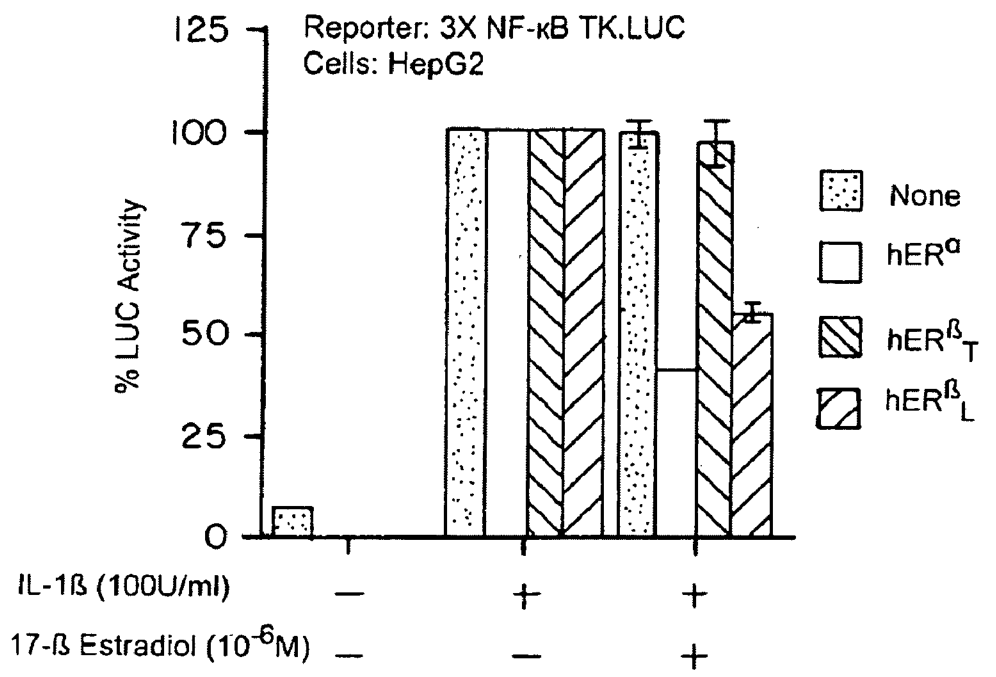
FIG. 7A is a graphic illustration of the effect of estradiol stimulation of full-length hERβ (hERβ$_L$) and truncated hERβ (hERβ$_T$) on NFkB activation in HepG2 cells. Cells were transfected with either hER$\beta_L$ or hER$\beta_T$ and co-transfected with a luciferase reporter plasmid containing three copies of an NFkB binding site (3×-NFkB TK.LUC) and a control β-galactosidase plasmid. Cells were stimulated with interleukin-1β and incubated in the absence or presence of estradiol, after which luciferase activity was measured and normalized to β-galactosidase activity.
FIG. 7B is a graphic illustration of luciferase activity in cells transfected with either hER$\beta_L$ or hER$\beta_T$ and co-transfected with a luciferase reporter plasmid lacking an NFkB binding site (TK.LUC).
Figure 7:
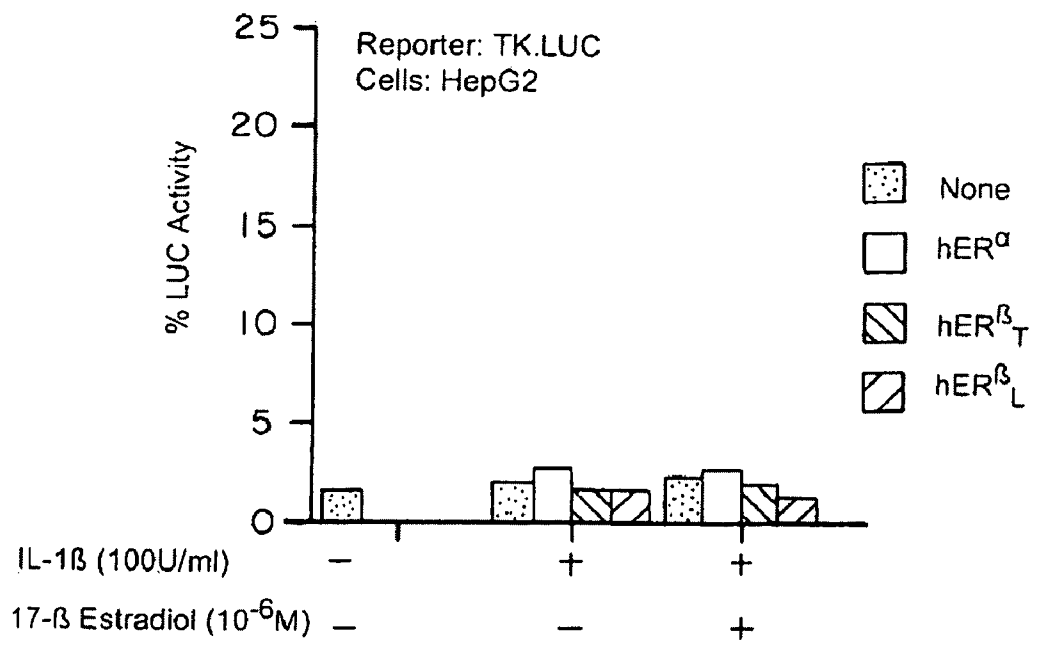

In a separate experiment, HepG2 cells were transfected with hERβ$_T$ or hERβ$_T$ as above, but the reporter gene consisted of three copies of an NFkB binding site upstream of the TK basal promoter. Transfected cells were incubated with or without interleukin-1β (IL-1β) to activate NFkB and/or with estradiol prior to luciferase determination. The results shown in FIG. 7 indicate that hERβ$_L$ was capable of attenuating the IL-1β-mediated NFkB transcriptional activation (to an extent similar to that observed with hERα) while hERβ$_T$ exhibited no inhibitory activity.

Figure 8:
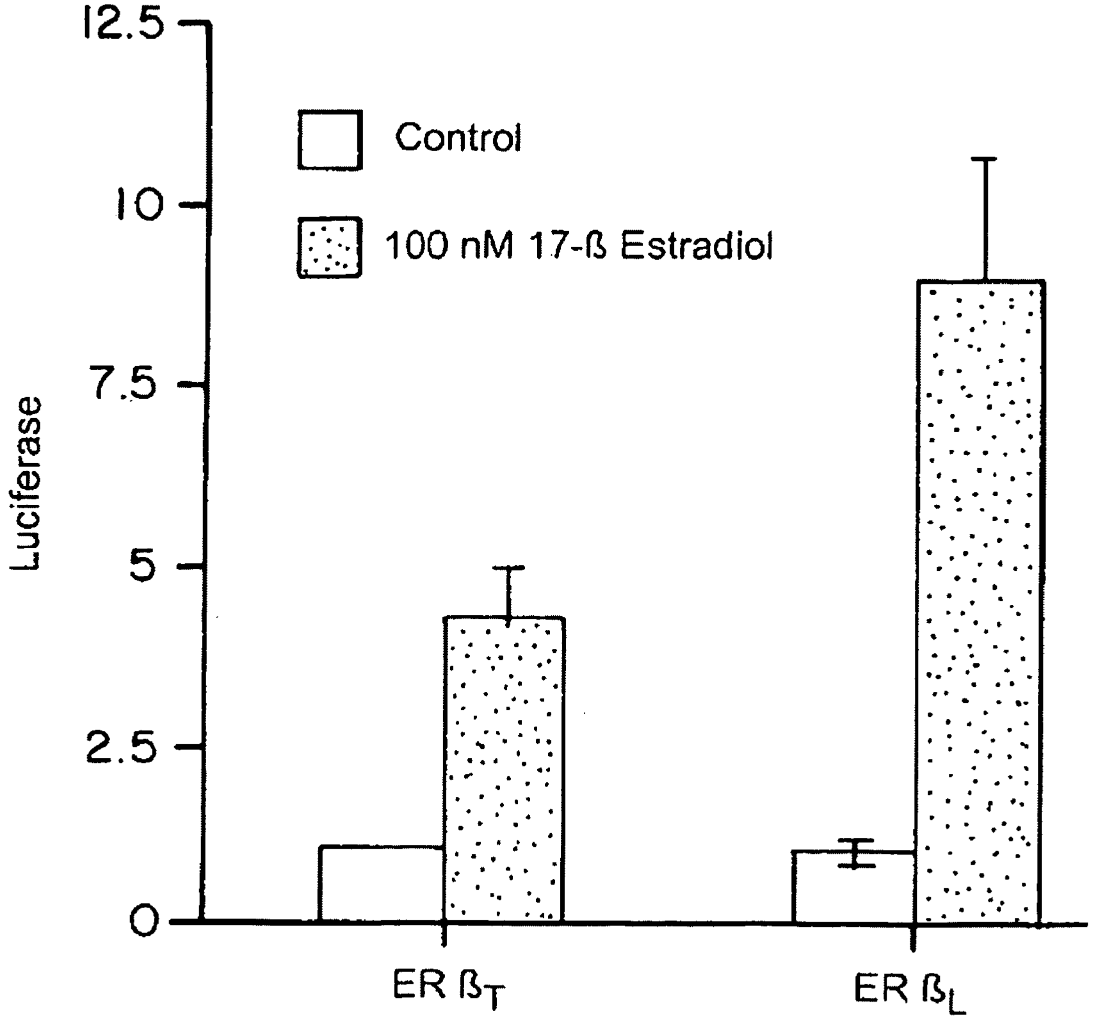
FIG. 8 is a graphic illustration of the transcriptional activation capacity of full-length hERβ (hER$\beta_L$) and truncated hERβ (hER$\beta_T$) expressed in HAECT-1 human endothelial cells. Cells were transfected with either hER$\beta_L$ or hER$\beta_T$ and co-transfected with a luciferase reporter plasmid containing an ERE (ERE.TK.LUC) or one lacking an ERE (TK.LUC). Cells were incubated in the absence or presence of estradiol, after which luciferase activity was measured. ERE TK.LUC values were normalized to TK.LUC values and are presented as mean±S.E. (n=4).

(ii) Human Endothelial Cells:

HAECT-1 cells (a clonal immortalized human aortic endothelia cell line derived by infection with Ad5 ori-SV40 ts A209) were transfected with pcDNA3hERβ$_T$ or pcDNA3-hERβ$_L$ and ERE-luciferase plasmids by electroporation. After 4 hours, the cells were treated overnight with or without 100 nM 17-β estradiol prior to luciferase activity measurements. The results shown in FIG. 8 indicate that hERβ$_L$ is 2–3 times more active than hERβ$_T$ in activating the ERE-reporter gene in the presence of estradiol. In independent experiments, cells transfected under identical conditions were monitored for their levels of estrogen receptors using a ligand binding assay. The results indicate that the increased activity of hERβ$_L$ relative to hERβ$_T$ is not due to an increase in receptor number or stability, and, further, that the 2–3 fold increment measured in the above experiment may be an underestimate of the true transactivational capacity of hERβ.

Figure 9:
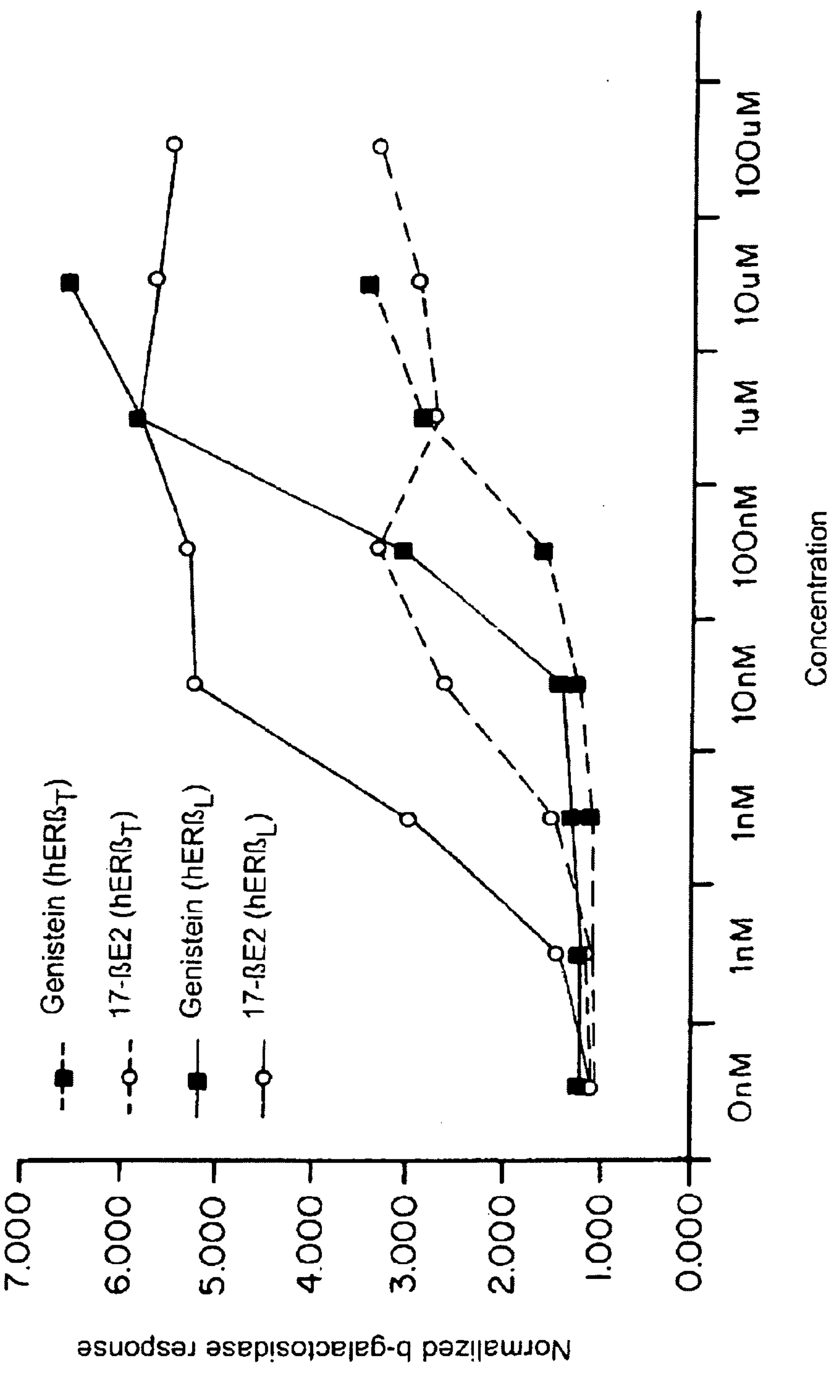
FIG. 9 is a graphic illustration of the effect of increasing doses of estrogens (17-β estradiol or genistein) on the transcriptional activation capacity of full-length hERβ (hER$\beta_L$) and truncated hERβ (hER$\beta_T$) expressed in *S. cerevisiae*. Cells were transformed with either hER$\beta_L$ or hER$\beta_T$ and co-transformed with a β-galactosidase reporter plasmid containing an ERE. Transformed cells were treated with estrogens for 3h and assayed for β-galactosidase activity.

(iii) Yeast:

*S. cerevisiae* strain BJ2168 (Yeast Genetic Stock Center, Berkeley Calif.) was co-transformed with an ERE-LacZ reporter plasmid (designated YRpE2) and yeast vectors expressing either hERβ$_L$ or hERβ$_T$ under the control of the yeast triose phosphate isomerase promoter in the yeast pYX242 vector (R&D Systems, Minneapolis Minn.). Transformed cells were grown in selective medium for 24 hours, after which they were treated in the presence or absence of increasing concentrations of either 17-β estradiol or the phytoestrogen Genistein (Research Biochemical International, Natick Mass.) for 3 hours prior to determination of β-galactosidase activity. The dose-response results shown in FIG. 9 indicate that the maximal level of estrogen-stimulated LacZ expression was 2-fold higher in hERβ$_L$-transformed cells relative to hERβ$_T$-transformed cells.

DNA, Vectors and Expression Systems

Many conventional techniques in molecular biology, microbiology, and recombinant DNA, are used in practicing the present invention. See, for example, Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis,* 1984, (M. L. Gait ed.); *Nucleic Acid Hybridization,* 1985, (Hames and Higgins); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, *A Practical Guide to Molecular Cloning*; the series, *Methods in Enzymology* (Academic Press, Inc.); *Gene Transfer Vectors for Mammalian Cells,* 1987 (J. H. Miller and M. P. Calos eds., Cold Spring Harbor Laboratory); and *Methods in Enzymology* Vol. 154 and Vol. 155 (Wu and Grossman, and Wu, eds., respectively).

The present invention encompasses purified, isolated, nucleic acid sequences encoding hERβ, including, e.g., the nucleotide sequence depicted in FIG. 3 SEQ ID NO:1 and subfragments derived therefrom, including without limitation transcriptional activation-competent fragments. An "isolated" or "purified" nucleic acid is a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

A nucleic acid that is "derived from" an hERβ sequence is a nucleic acid sequence that corresponds to a region of the sequence, sequences that are homologous or complementary to the sequence, and "sequence-conservative variants" and "function-conservative variants". Sequence-conservative variants are those in which a change of one or more nucleotides in a given codon position results in no alteration in the amino acid encoded at that position. Function-conservative variants are those in which the amino acid sequence of hERβ has been changed without altering the overall conformation and transcriptional activation function of the hERβ polypeptide, including, but not limited to, replacement of an amino acid with one having similar physico-chemical properties (such as, for example, acidic, basic, hydrophobic, and the like). A large number of candidate function-conservative hERβ variants, as well as fragments of hERβ that retain transcriptional activation activity, can be prepared using routine recombinant DNA manipulations as well as random or site-directed mutagenesis techniques. Furthermore, hERβ-derived variants or fragments that exhibit transcriptional activation activity can be identified using routine experimentation by employing the methods described herein, e.g., by co-expression with an appropriate reporter gene followed by measurement of reporter gene transcription in the presence and absence of an estrogen.

In another embodiment, the present invention encompasses isolated, purified, nucleic acids comprising nucleotides 94–229 of the sequence depicted in FIG. 3, SEQ ID NO:1, which encode amino acids 1–45 of hERβ, and sequence-conservative variants thereof.

The nucleic acids of the present invention include purine- and pyrimidine-containing polymers of any length, either polyribonucleotides or polydeoxyribonucleotides or mixed polyribo-polydeoxyribo nucleotides. This includes single- and double-stranded molecules, i.e., DNA—DNA, DNA-RNA and RNA—RNA hybrids, as well as "protein nucleic acids" (PNA) formed by conjugating bases to an amino acid backbone. This also includes nucleic acids containing modified bases.

The nucleic acids may be isolated directly from cells. Alternatively, PCR can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising hERβ-encoding sequences or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression. The encoded hERβ-derived polypeptides may be expressed by using many known vectors, such as pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication systems for cloning or expression, one or more markers for selection in the host, e.g. antibiotic resistance, and one or more expression cassettes. The inserted hERβ-encoding sequences may be synthesized by standard methods, isolated from natural sources, or prepared as hybrids, etc. Ligation of the hERβ-encoding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, viral vector-mediated DNA delivery, fungal infection, microinjection, microprojectile, or other established methods.

Appropriate host cells included bacteria, archebacteria, fungi, especially yeast, and plant and animal cells, especially mammalian cells. Of particular interest are *E. coli, B. Subtilis, Saccharomyces cerevisiae, Saccharomyces carlsbergensis, Schizosaccharomyces pombi*, SF9 cells, C129 cells, 293 cells, *Neurospora*, and HepG2 cells, CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced hERβ-derived peptides and polypeptides.

Advantageously, vectors may also include a transcription regulatory element (i.e., a promoter) operably linked to the hERβ portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include triose phosphate isomerase promoter, 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding hERβ-derived polypeptides may also be introduced into cells by recombination events. For example, such a sequence can be introduced into a cell, and thereby effect homologous recombination at the site of an endogenous gene or a sequence with substantial identity to the gene. Other recombination-based methods such as non-homologous recombinations or deletion of endogenous genes by homologous recombination may also be used.

The nucleic acids of the present invention find use as templates for the recombinant production of hERβ-derived peptides or polypeptides.

hERβ-Derived Polypeptides

The present invention encompasses purified hERβ-derived polypeptides comprising amino acids 1–45 of hERβ and further comprising all or part of the amino acid sequence depicted in FIG. 4, SEQ ID NO:2, and function-conservative variants thereof, i.e., variants that exhibit estrogen-induced transcriptional activation activity. Also encompassed by the invention are peptides comprising amino acids 1–45 of SEQ ID NO:2 and function-conservative variants thereof.

Nucleic acids comprising hERβ-coding sequences can be used to direct the expression of hERβ-derived polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of Matteucci et al., 1981*, J. Am. Chem. Soc.* 103:3185, the method of Yoo et al., 1989*, J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed hERβ sequences, may be isolated from wild-type or mutant human cells, or from heterologous organisms or cells (including, but not limited to, bacteria, fungi, insect, plant, and mammalian cells) into which an hERβ-derived protein-coding sequence has been introduced and expressed. Furthermore, the polypeptides may be part of recombinant fusion proteins.

Polypeptides may be chemically synthesized by commercially available automated procedures, including, without limitation, exclusive solid phase synthesis, partial solid phase methods, fragment condensation or classical solution synthesis. The polypeptides are preferably prepared by solid phase peptide synthesis as described by Merrifield, 1963*, J. Am. Chem. Soc.* 85:2149.

"Isolation" or "purification" of an hERβ-derived polypeptide refers to the isolation of the polypeptide in a form that allows its transcriptional activation activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the hERβ-derived protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against an hERβ-derived protein or against peptides derived therefrom can be used as purification reagents. Other purification methods are possible.

The present invention also encompasses derivatives and homologues of hERβ-encoded polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

hERβ-specific Antibodies

The present invention encompasses antibodies that specifically recognize hERβ-derived peptides and polypeptides, including without limitation antibodies that recognize hERβ but not, e.g., hERα, and those that recognize $hER\beta_L$ but not $hER\beta_L$. Such hERβ-specific antibodies can be used conventionally, e.g., as diagnostic reagents or as reagents for purification of hERβ-derived polypeptides. Other uses include immunocytochemical localization of hERβ; gel shift assays; and "pull-down" experiments to identify protein co-activators associated with hERβ.

hERβ-specific antibodies according to the present invention include polyclonal and monoclonal antibodies. The antibodies may be elicited in an animal host by immunization with hERβ immunogenic components or may be formed by in vitro immunization (sensitization) of immune cells. The immunogenic components used to elicit the production of antibodies may be isolated from any cell source or may be chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and $F(ab)_2$ fragments of antibodies. Methods for the production of all of the above types of antibodies and derivatives are well-known in the art. For example, techniques for producing and processing polyclonal antisera are disclosed in Mayer and Walker, 1987, *Immunochemical Methods in Cell and Molecular Biology*, (Academic Press, London). The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Schreier et al., 1980, *Hybridoma Techniques*. Panels of monoclonal antibodies produced against hERβ epitopes can be screened for various properties; i.e., for isotype, epitope affinity, etc.

Antibodies against hERβ-derived immunogenic components can be used, unlabeled or labeled by standard methods, as the basis for immunoassays. The particular label used will depend upon the type of immunoassay used. Examples of labels that can be used include but are not limited to radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydrophthal-azinediones; and enzymes such as horseradish peroxidase, alkaline phosphatase, lysozyme and glucose-6-phosphate dehydrogenase.

Applications

The methods and compositions of the present invention can be used to identify compounds that interact with hERβ, either to activate or to inhibit its transcriptional activation function. Such compounds include, without limitation, co-activator proteins, as well as estrogens and other steroids, steroid-like molecules, or non-steroid-like molecules that act as agonists or antagonists. Screening methods can also be used to identify tissue-specific estrogens.

Identification of hERβ-interactive compounds can be achieved by cell-free or cell-based assays. In one set of embodiments, purified hERβis contacted with a labelled ligand, such as, e.g., 17-β estradiol, in the presence of test compounds to form test reactions, and in the absence of test compounds to form control reactions. The labelled moiety may comprise a radiolabel (such as, e.g., $^{3}H$ or $^{125}I$) or a fluorescent molecule. Incubation is allowed to proceed for a sufficient time and under appropriate conditions to achieve specific binding, after which binding of labelled estradiol to hERβ is measured (by monitoring, e.g., radioactivity, flurorescence, or fluorescence polarization). In one embodiment, hERβproduced in *E. coli* (as described in Example 1 below) is adsorbed to the wells of a microtiter dish and incubated with [$^{3}H$]-17β, estradiol in the absence or presence of test compounds (see, e.g., Example 2 below). Alternatively, soluble receptor is incubated with the labelled ligand in the absence or presence of test compounds, and bound ligand is separated from free ligand, either by filtration on glass fiber filters or by using dextran-coated charcoal. See, e.g., Hulme, ed., *Receptor-ligand Interactions: A Practical Approach*, IRL Press, NY, 1992).

Whole cell binding assays may also be used in which bound ligand is separated from free ligand by rinsing. Cells used in these assays may either contain endogenous receptor, or may overexpress the receptor subsequent to stable or transient transfection or infection of an hERβ, gene or cDNA. Non-limiting examples of suitable cells include COS cells, Hela cells, CHO cells, human umbilical vein endothelial cells (HUVEC), and yeast. Once a compound has been identified as an hERβ-interactive compound by its binding activity, further in vivo and in vitro tests may be performed to determine the nature and extent of activity, i.e., as an agonist or antagonist (see below).

hERβ-interactive compounds may also be identified using cell-based assays that measure transcriptional activation or suppression of endogenous or transfected estrogen-responsive genes. For example, agonists (such as, e.g., 17β-estradiol) block interleukin-1β induction of endogenous E-selectin in primary human umbilical vein endothelial cells (HUVEC) that express hERβ. Antagonists (such as, e.g., ICI-182780) block the agonist activity of 17β-estradiol. Non-limiting examples of other suitable endogenous estrogen-responsive promoter elements include those that regulate endothelin-1 (ET-1); HDL receptor (scavenger receptor type II); and enzymes involved in coagulation and fibrinolysis (such as, e.g., plasminogen activator inhibitor-1 and complement C3). Any promoter element that responds to estrogen may be used as an appropriate target, including, e.g., the NFkB binding site or the apolipoprotein A1 gene enhancer sequence.

In one set of embodiments, appropriate host cells are transfected with an expression vector encoding hERβ and the transfectants are incubated with or without estradiol in the presence or absence of test compounds. hERβ activity is assessed by measuring transcriptional activation of the target sequence. This may be achieved by detection of mRNA (using, e.g., Northern blot analysis) and/or by detection of the protein (using, e.g., immunoassays or functional assays). If activation of the target sequence initiates a biochemical cascade, downstream biological events may also be measured to quantify hERβ activity. hERβ-interactive compounds are identified as those that positively or negatively influence target sequence activation.

In another set of embodiments, appropriate host cells (preferably, bacterial or yeast cells) are co-transfected with an expression vector encoding hERβ and a reporter plasmid containing a reporter gene downstream of one or more estrogen response elements (EREs). Transfected cells are incubated with or without estradiol in the presence of absence of test compounds, after which hERβ activity is determined by measuring expression of the reporter gene. In a preferred embodiment, hERβ activity is monitored visually. Non-limiting examples of suitable reporter genes include luciferase, chloramphenicol acetyl transferase (CAT), and green fluorescence protein.

Preferably, the methods of the present invention are adapted to a high-throughput screen, allowing a multiplicity of compounds to be tested in a single assay. Candidate estrogens and estrogen-like compounds include without limitation diethylstilbesterol, genistein, and estrone. Other hERβ-interactive compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., *TibTech* 14:60, 1996). hERβ binding assays according to the present invention are advantageous in accommodating many different types of solvents and thus allowing the testing of compounds from many sources.

Compounds identified as hERβ agonists or antagonists using the methods of the present invention may be modified to enhance potency, efficacy, uptake, stability, and suitability for use in therapeutic applications, etc. These modifications are achieved and tested using methods well-known in the art.

DESCRIPTION OF THE PREFERRED EMBODIMENTS

The following examples are intended to illustrate the present invention without limitation.

EXAMPLE 1

High-level Expression of Human hERB in *E. coli*

Human hERβ according to the present invention is overexpressed in *E. coli* strain BL21(DE3) using, for example, the pET15B vector. A 10-ml overnight culture is used to inoculate 1 liter LB medium containing 100 μg/ml ampicillin. Cultures are grown at 37° C. and then induced by the addition of 1 mM IPTG. After an additional incubation for 2h at 25° C., cells are harvested by centrifugation at 10,000× G for 30 minutes and resuspended in 100 ml of a buffer containing 50 mM Tris-HCl, pH 7.4–150 mM NaCl. Cells are lysed using a French press, and insoluble material is pelleted by centrifugation. The supernatant solution is recovered and stored at −70° C.

EXAMPLE 2

Estrogen Receptor-d Ligand Binding Assay

For determining the ability of a particular compound to bind hERβ, 100 μl of the receptor preparation described in Example 1 above, diluted in assay buffer (Dulbecco's phosphate buffered saline (Gibco #14200-075) supplemented with 1 mM EDTA), is added to each well of a high-binding masked microtiter plate (Wallac #1450-511, Gaithersburg Md.). 10 μl of test compound (or vehicle) and 10 μl of $[^3H]$-17β-estradiol are added to each well, and the plate is incubated at room temperature for 4–6 hours. Unbound material is aspirated, and the plate is washed three times with 300 μl of assay buffer. Then, 150 μl of scintillation cocktail (Optiphase Supermix, Wallac #1200-439) is added per well, and the plate is sealed and agitated for at least 5 min. Bound radioactivity is measured by scintillation counting.

Test compounds are initially tested at a concentration of 1.5 μg/ml (approximately 5 μM for a compound having a molecular mass of 300). Positive compounds are then retested at a number of different concentrations to determine the $IC_{50}$.

Data are expressed as percent inhibition of specific binding. Exploratory data analysis (EDA) is performed on raw data to check for non-normality and non-homogeneity of variance. The maximum likelihood Box-Cox transformation, which maximizes the normality, homogeneity of variance, and goodness of fit of the data, is then obtained. Based on the result, the appropriate transformation of the data (no transformation, square root transformation, or logarithmic transformation) is used for model fitting. The Huber M-estimator is used to down weight any outlying transformed observations for analysis of variance and dose-response curve fitting.

For ANOVA, multiple comparisons LSD p-values are computed. Re-transformed summary statistics (mean, s.d, s.e.m.) are obtained for each treatment group.

For dose-response curve fitting, a four parameter logistic model on the transformed, weighted data are fit. The four parameters are min, max, slope, and ED50, where ED50 is defined as the dose which corresponds to midway between the estimated max and min. All of the parameters and confidence intervals are re-transformed back to the original units of the data. A further transformation into percent inhibition (using estimated min and max) is performed.

Using this assay, the following values were obtained for reference compounds:

| | $IC_{50}$ | 95% confidence limits |
|---|---|---|
| 17β-estradiol | 6.7 nM | 6–7.5 nM |
| diethylstilbestrol | 21 nM | 14–31 nM |
| genistein | 1.6 nM | 1.4–1.8 nM |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

The invention claimed is:

1. An isolated nucleic acid comprising the sequence depicted in FIG. 3, SEQ ID NO:1, or an RNA sequence corresponding thereto, wherein said sequence is flanked by one or more heterologous sequences.

2. The nucleic acid of claim 1, wherein said nucleic acid is DNA.

3. The nucleic acid of claim 1, wherein said nucleic acid is RNA.

4. A recombinant DNA vector comprising the nucleic acid of claim 1.

5. A recombinant DNA vector comprising the nucleic acid of claim 1 operably linked to a transcription regulatory element.

6. An isolated host cell comprising the DNA vector of claim 5.

7. The cell of claim 6 which is selected from the group consisting of bacterial, fungal, plant, insect, and mammalian cells.

8. A method for producing a polypeptide, which method comprises incubating the cell of claim 6 under conditions that permit expression of a polypeptide encoded by the nucleic acid.

9. The method of claim 8, which further comprises:

(a) harvesting said incubated cells to produce a cell fraction and a medium fraction; and (b) recovering the polypetide from the cell fraction, the medium fraction, or both.

* * * * *

SEQUENCE LISTING

<160> NUMBER OF SEQ ID NOS: 13

<210> SEQ ID NO 1
<211> LENGTH: 1686
<212> TYPE: DNA
<213> ORGANISM: Human

<400> SEQUENCE: 1

```
cagccattat acttgcccac gaatctttga gaacattata atgacctttg tgcctcttct     60

tgcaaggtgt tttctcagct gctatctcaa gacatggata taaaaaactc accatctagc    120

cttaattctc cttcctccta caactgcagt caatccatct taccccctgga gcacggctcc   180

atatacatac cttcctccta tgtagacagc caccatgaat atccagccat gacattctat    240

agccctgctg tgatgaatta cagcattccc agcaatgtca ctaacttgga aggtgggcct    300

ggtcggcaga ccacaagccc aaatgtgttg tggccaacac ctgggcacct ttctccttta    360

gtggtccatc gccagttatc acatctgtat gcggaacctc aaaagagtcc ctggtgtgaa    420

gcaagatcgc tagaacacac cttacctgta aacagagaga cactgaaaag gaaggttagt    480

gggaaccgtt gcgccagccc tgttactggt ccaggttcaa agagggatgc tcacttctgc    540

gctgtctgca gcgattacgc atcgggatat cactatggag tctggtcgtg tgaaggatgt    600

aaggcctttt ttaaaagaag cattcaagga cataatgatt atatttgtcc agctacaaat    660

cagtgtacaa tcgataaaaa ccggcgcaag agctgccagg cctgccgact tcggaagtgt    720

tacgaagtgg gaatggtgaa gtgtggctcc cggagagaga gatgtgggta ccgccttgtg    780

cggagacaga gaagtgccga cgagcagctg cactgtgccg gcaaggccaa gagaagtggc    840

ggccacgcgc cccgagtgcg ggagctgctg ctggacgccc tgagccccga gcagctagtg    900

ctcaccctcc tggaggctga gccgccccat gtgctgatca gccgccccag tgcgcccttc    960

accgaggcct ccatgatgat gtccctgacc aagttggccg acaaggagtt ggtacacatg   1020

atcagctggg ccaagaagat tcccggcttt gtggagctca gcctgttcga ccaagtgcgg   1080

ctcttggaga gctgttggat ggaggtgtta atgatggggc tgatgtggcg ctcaattgac   1140

caccccggca agctcatctt tgctccagat cttgttctgg acagggatga ggggaaatgc   1200

gtagaaggaa ttctggaaat ctttgacatg ctcctggcaa ctacttcaag gtttcgagag   1260

ttaaaactcc aacacaaaga atatctctgt gtcaaggcca tgatcctgct caattccagt   1320
```

-continued

```
atgtaccctc tggtcacagc gacccaggat gctgacagca gccggaagct ggctcacttg   1380

ctgaacgccg tgaccgatgc tttggtttgg gtgattgcca agagcggcat ctcctcccag   1440

cagcaatcca tgcgcctggc taacctcctg atgctcctgt cccacgtcag gcatgcgagt   1500

aacaagggca tggaacatct gctcaacatg aagtgcaaaa atgtggtccc agtgtatgac   1560

ctgctgctgg agatgctgaa tgcccacgtg cttcgcgggt gcaagtcctc catcacgggg   1620

tccgagtgca gcccggcaga ggacagtaaa agcaaagagg gctcccagaa cccacagtct   1680

cagtga                                                              1686


<210> SEQ ID NO 2
<211> LENGTH: 530
<212> TYPE: PRT
<213> ORGANISM: Human

<400> SEQUENCE: 2

Met Asp Ile Lys Asn Ser Pro Ser Ser Leu Asn Ser Pro Ser Ser Tyr
 1               5                  10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285

Phe Thr Glu Ala Ser Met Met Met Ser Leu Thr Lys Leu Ala Asp Lys
    290                 295                 300
```

-continued

```
Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430

Val Thr Asp Ala Leu Val Trp Val Ile Ala Lys Ser Gly Ile Ser Ser
        435                 440                 445

Gln Gln Gln Ser Met Arg Leu Ala Asn Leu Leu Met Leu Leu Ser His
    450                 455                 460

Val Arg His Ala Ser Asn Lys Gly Met Glu His Leu Leu Asn Met Lys
465                 470                 475                 480

Cys Lys Asn Val Val Pro Val Tyr Asp Leu Leu Leu Glu Met Leu Asn
                485                 490                 495

Ala His Val Leu Arg Gly Cys Lys Ser Ser Ile Thr Gly Ser Glu Cys
            500                 505                 510

Ser Pro Ala Glu Asp Ser Lys Ser Lys Glu Gly Ser Gln Asn Pro Gln
        515                 520                 525

Ser Gln
    530
```

<210> SEQ ID NO 3
<211> LENGTH: 12
<212> TYPE: PRT
<213> ORGANISM: Rat

<400> SEQUENCE: 3

```
Met Thr Phe Tyr Ser Pro Ala Val Met Asn Tyr Ser
 1               5                  10
```

<210> SEQ ID NO 4
<211> LENGTH: 10
<212> TYPE: PRT
<213> ORGANISM: Human

<400> SEQUENCE: 4

```
Gly Tyr Ser Pro Ala Val Met Asn Tyr Ser
 1               5                  10
```

<210> SEQ ID NO 5
<211> LENGTH: 45
<212> TYPE: DNA
<213> ORGANISM: Artificial Sequence
<220> FEATURE:
<223> OTHER INFORMATION: PCR Primer

<400> SEQUENCE: 5

```
ggaagcttgt cgaccatcat gaccggctat agccctgctg tgatg                45
```

-continued

<210> SEQ ID NO 6
<211> LENGTH: 40
<212> TYPE: DNA
<213> ORGANISM: Artificial Sequence
<220> FEATURE:
<223> OTHER INFORMATION: PCR Primer

<400> SEQUENCE: 6
ggatctagag tcgacgcgtc actgagactg agggttctgg 40

<210> SEQ ID NO 7
<211> LENGTH: 4
<212> TYPE: PRT
<213> ORGANISM: Human

<400> SEQUENCE: 7

Met Thr Gly Tyr
1

<210> SEQ ID NO 8
<211> LENGTH: 17
<212> TYPE: DNA
<213> ORGANISM: Human

<400> SEQUENCE: 8
ccatcatgac cggctat 17

<210> SEQ ID NO 9
<211> LENGTH: 23
<212> TYPE: DNA
<213> ORGANISM: Artificial Sequence
<220> FEATURE:
<223> OTHER INFORMATION: PCR Primer

<400> SEQUENCE: 9
ctggtaagtt tagtcttttt gtc 23

<210> SEQ ID NO 10
<211> LENGTH: 25
<212> TYPE: DNA
<213> ORGANISM: Artificial Sequence
<220> FEATURE:
<223> OTHER INFORMATION: PCR Primer

<400> SEQUENCE: 10
gcttcacacc aaggactctt ttgag 25

<210> SEQ ID NO 11
<211> LENGTH: 26
<212> TYPE: DNA
<213> ORGANISM: Artificial Sequence
<220> FEATURE:
<223> OTHER INFORMATION: PCR Primer

<400> SEQUENCE: 11
gttggccaca acacatttgg gcttgt 26

<210> SEQ ID NO 12
<211> LENGTH: 27
<212> TYPE: DNA
<213> ORGANISM: Artificial Sequence
<220> FEATURE:
<223> OTHER INFORMATION: PCR Primer

<400> SEQUENCE: 12

-continued

```
ccatcctaat acgactcact atagggc                                        27


<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13

actcactata gggctcgagc ggc                                            23
```